United States Patent
Iwase et al.

(10) Patent No.: US 10,360,683 B2
(45) Date of Patent: Jul. 23, 2019

(54) IMAGE PROCESSING APPARATUS, IMAGE PROCESSING METHOD, AND PROGRAM

(71) Applicant: CANON KABUSHIKI KAISHA, Tokyo (JP)

(72) Inventors: Yoshihiko Iwase, Yokohama (JP); Makoto Sato, Tokyo (JP)

(73) Assignee: CANON KABUSHIKI KAISHA, Tokyo (JP)

(*) Notice: Subject to any disclaimer, the term of this patent is extended or adjusted under 35 U.S.C. 154(b) by 107 days.

(21) Appl. No.: 15/525,924

(22) PCT Filed: Oct. 14, 2015

(86) PCT No.: PCT/JP2015/005191
§ 371 (c)(1),
(2) Date: May 10, 2017

(87) PCT Pub. No.: WO2016/075868
PCT Pub. Date: May 19, 2016

(65) Prior Publication Data
US 2017/0323446 A1 Nov. 9, 2017

(30) Foreign Application Priority Data
Nov. 12, 2014 (JP) .................. 2014-229912

(51) Int. Cl.
*G06T 7/11* (2017.01)
*A61B 3/10* (2006.01)
(Continued)

(52) U.S. Cl.
CPC ............ *G06T 7/11* (2017.01); *A61B 3/102* (2013.01); *G03B 42/08* (2013.01); *G06F 9/30* (2013.01); *G06T 2207/20212* (2013.01)

(58) Field of Classification Search
CPC . A61B 3/102; G06T 7/11; G06T 2207/20212; G03B 42/08; G06F 9/30
(Continued)

(56) References Cited

U.S. PATENT DOCUMENTS
2014/0121506 A1 5/2014 Iwase

FOREIGN PATENT DOCUMENTS
EP 2243420 A1 10/2010
JP 2014-045905 A 3/2014
(Continued)

OTHER PUBLICATIONS

Bernhard Baumann et al. ; "Segmentation and quantification of retinal lesions in age-related macular degeneration using polarization-sensitive optical coherence tomography;" Journal of Biomedical Optics, vol. 15, No. 6, pp. 061704-1-061704-9; Nov./Dec. 2010.

*Primary Examiner* — Daniel G Mariam
(74) *Attorney, Agent, or Firm* — Canon U.S.A., Inc. IP Division

(57) ABSTRACT

An image processing apparatus includes a detection unit configured to detect a depolarized region in a polarization tomographic image of a subject's eye, an estimation unit configured to estimate a curve using the extracted depolarized region, a discrimination unit configured to discriminate the extracted depolarized region as a region including the estimated curve and a region which is discontinuous with the region including the estimated curve, and a correcting unit configured to correct at least a portion of a result of the discrimination representing the discontinuous region to a result of discrimination representing another region.

27 Claims, 13 Drawing Sheets

(51) Int. Cl.
*G03B 42/08* (2006.01)
*G06F 9/30* (2018.01)

(58) Field of Classification Search
USPC .......................................... 382/131–132, 173
See application file for complete search history.

(56) References Cited

FOREIGN PATENT DOCUMENTS

| | | |
|---|---|---|
| WO | 2010/080576 A1 | 7/2010 |
| WO | 2010/122118 A1 | 10/2010 |
| WO | 2013/165614 A1 | 11/2013 |

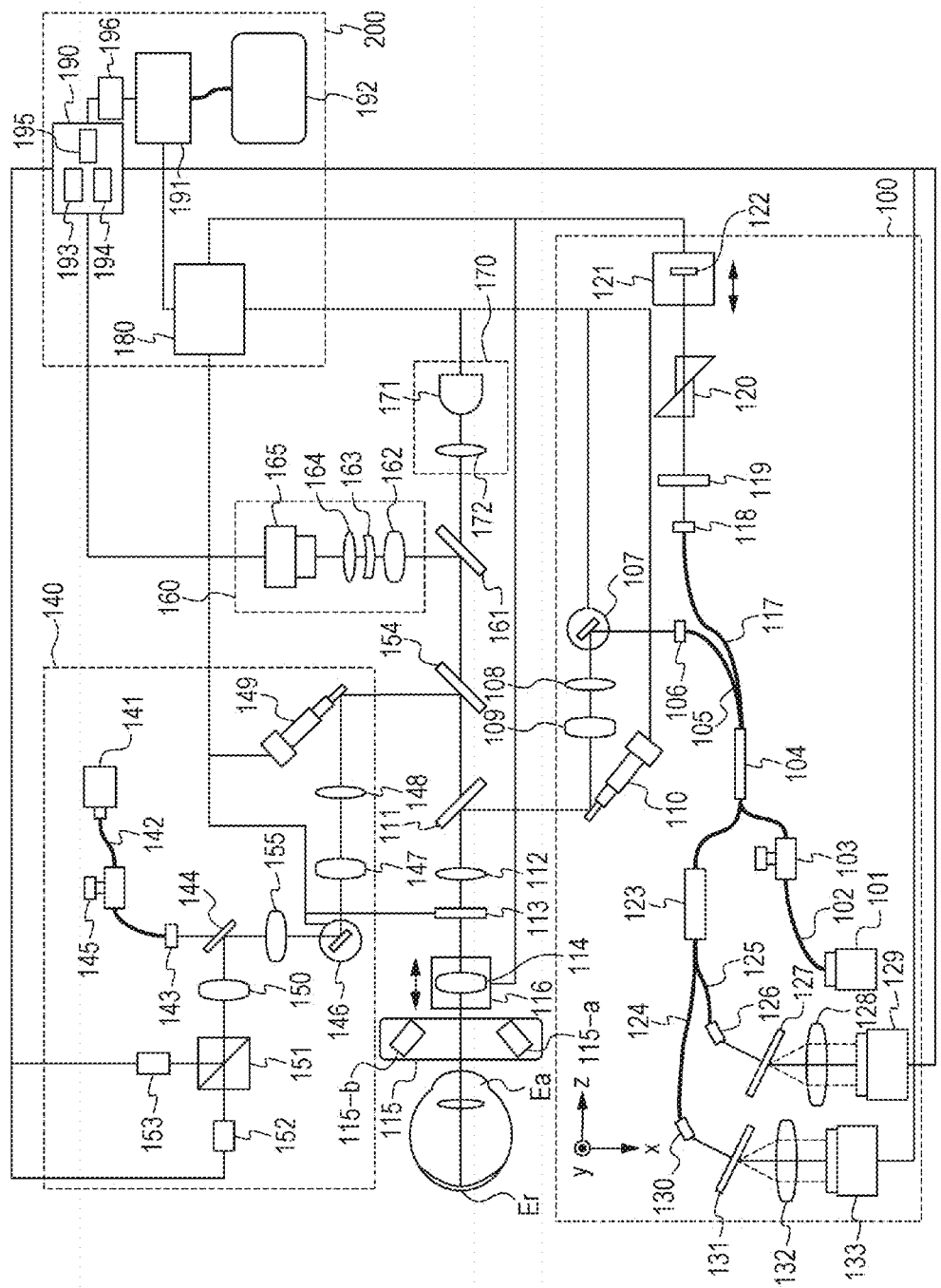
[Fig. 1]

[Fig. 2A]
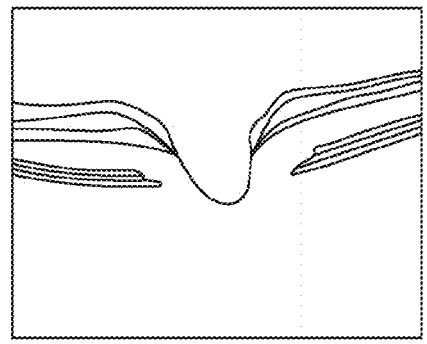
[Fig. 2B]
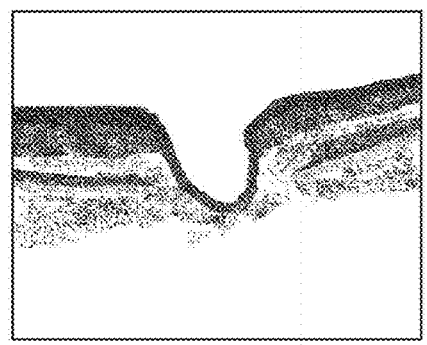
[Fig. 2C]
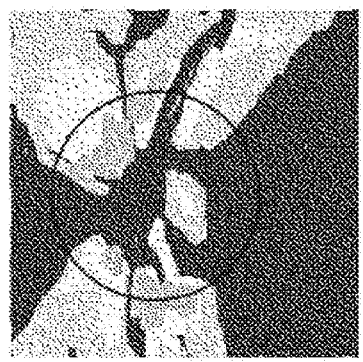

[Fig. 2D]
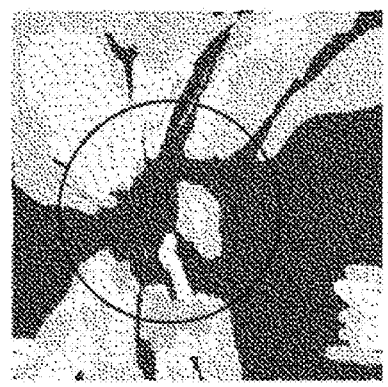
[Fig. 2E]
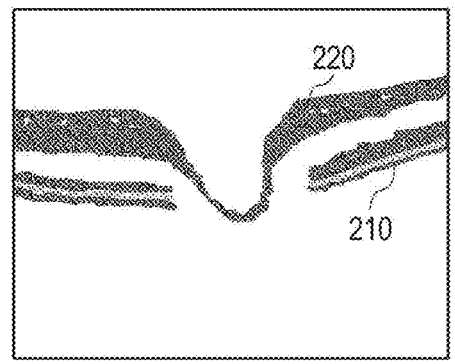

[Fig. 3A]
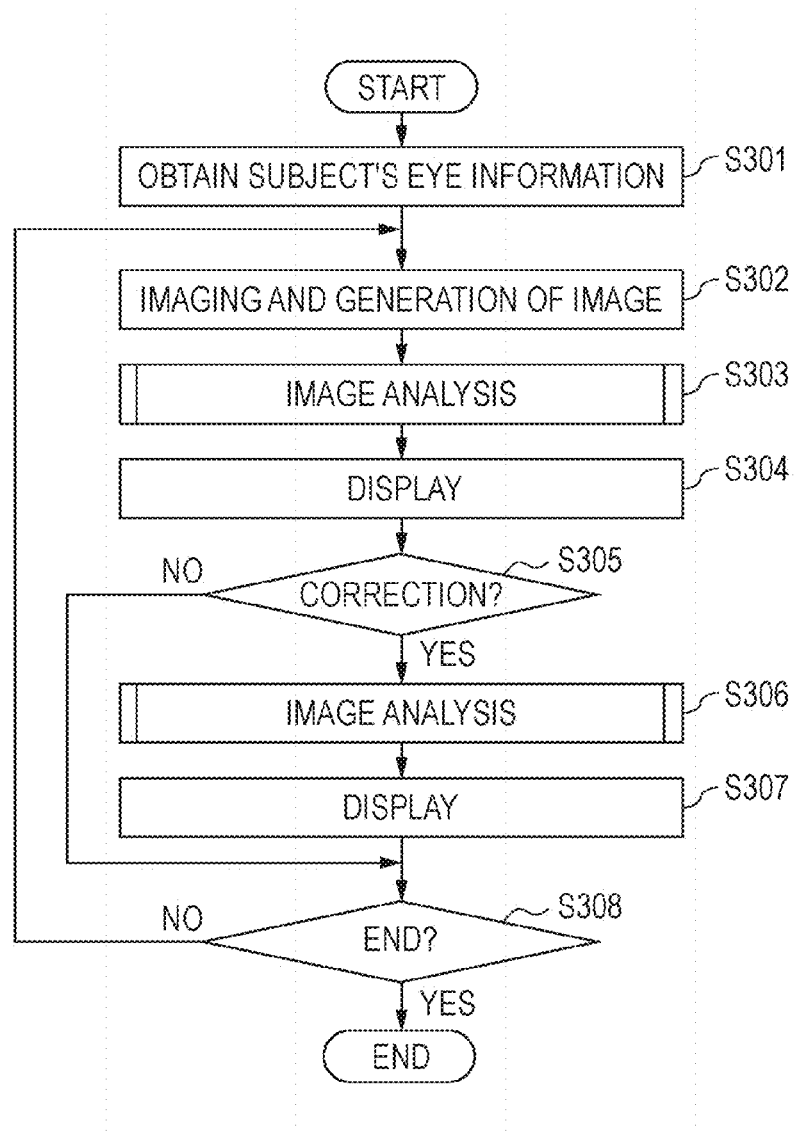

[Fig. 3B]
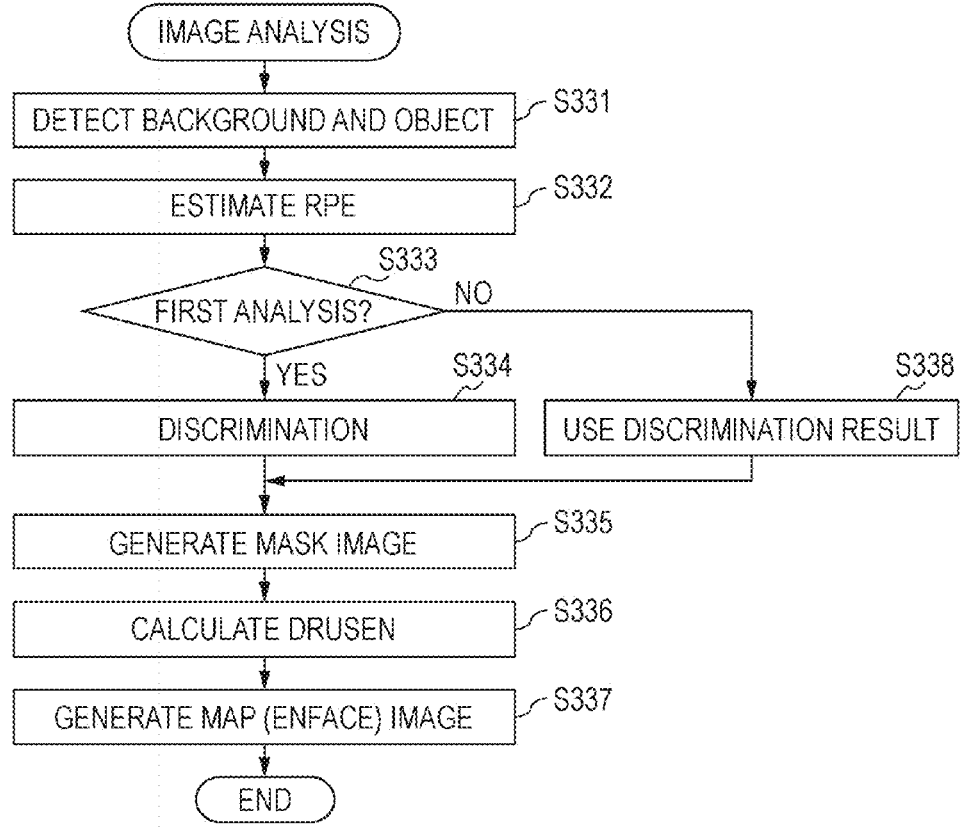
[Fig. 4A]
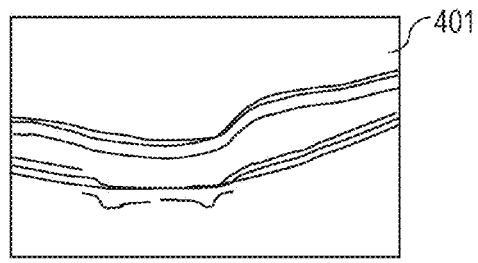

[Fig. 4B]
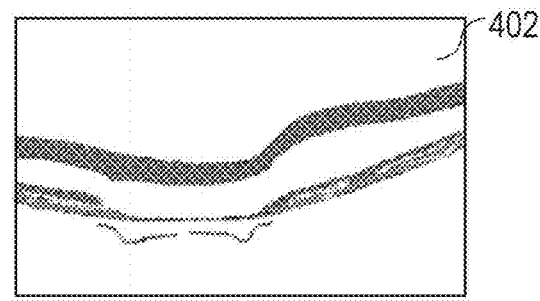
[Fig. 4C]
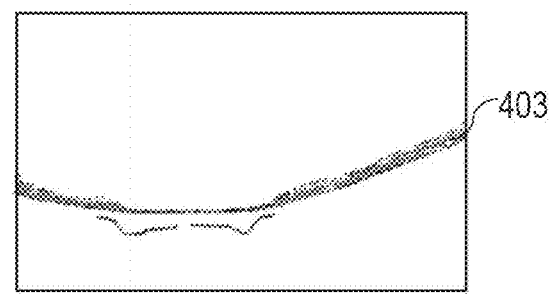
[Fig. 4D]
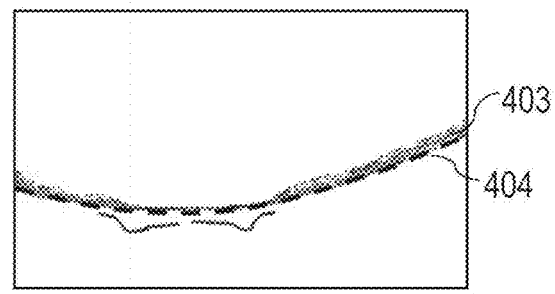

[Fig. 4E]
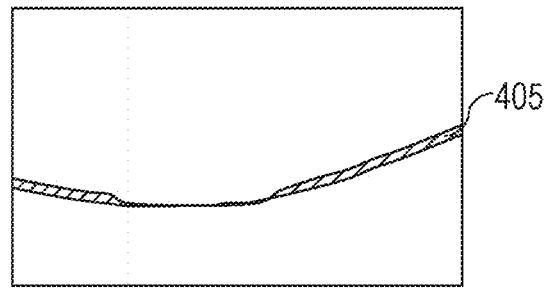
[Fig. 4F]
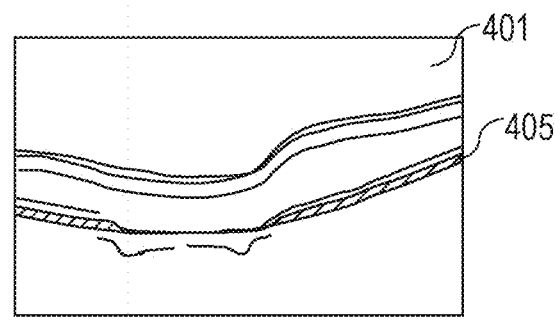
[Fig. 5A]
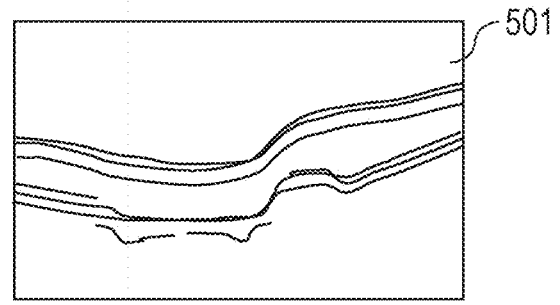

[Fig. 5B]
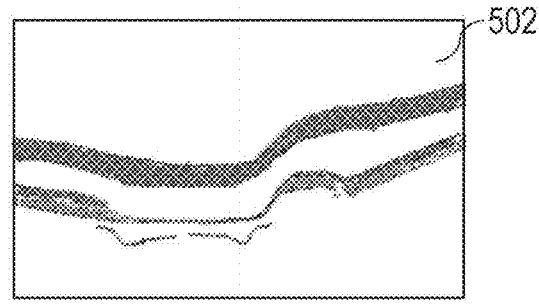
[Fig. 5C]
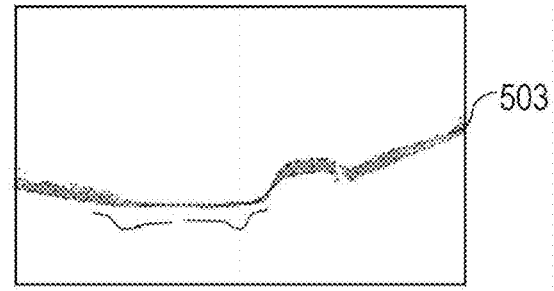
[Fig. 5D]
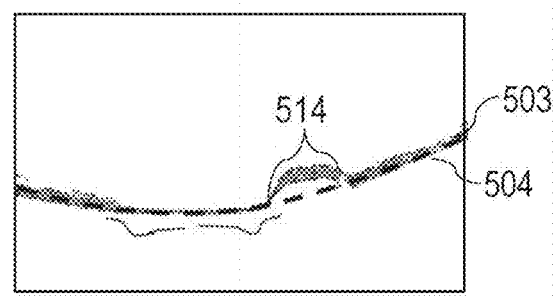

[Fig. 5E]
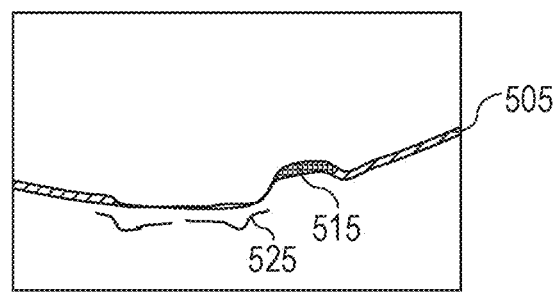
[Fig. 5F]
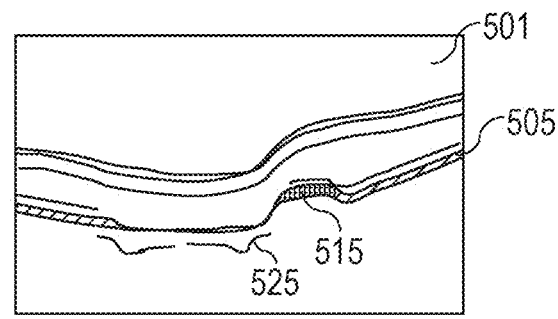

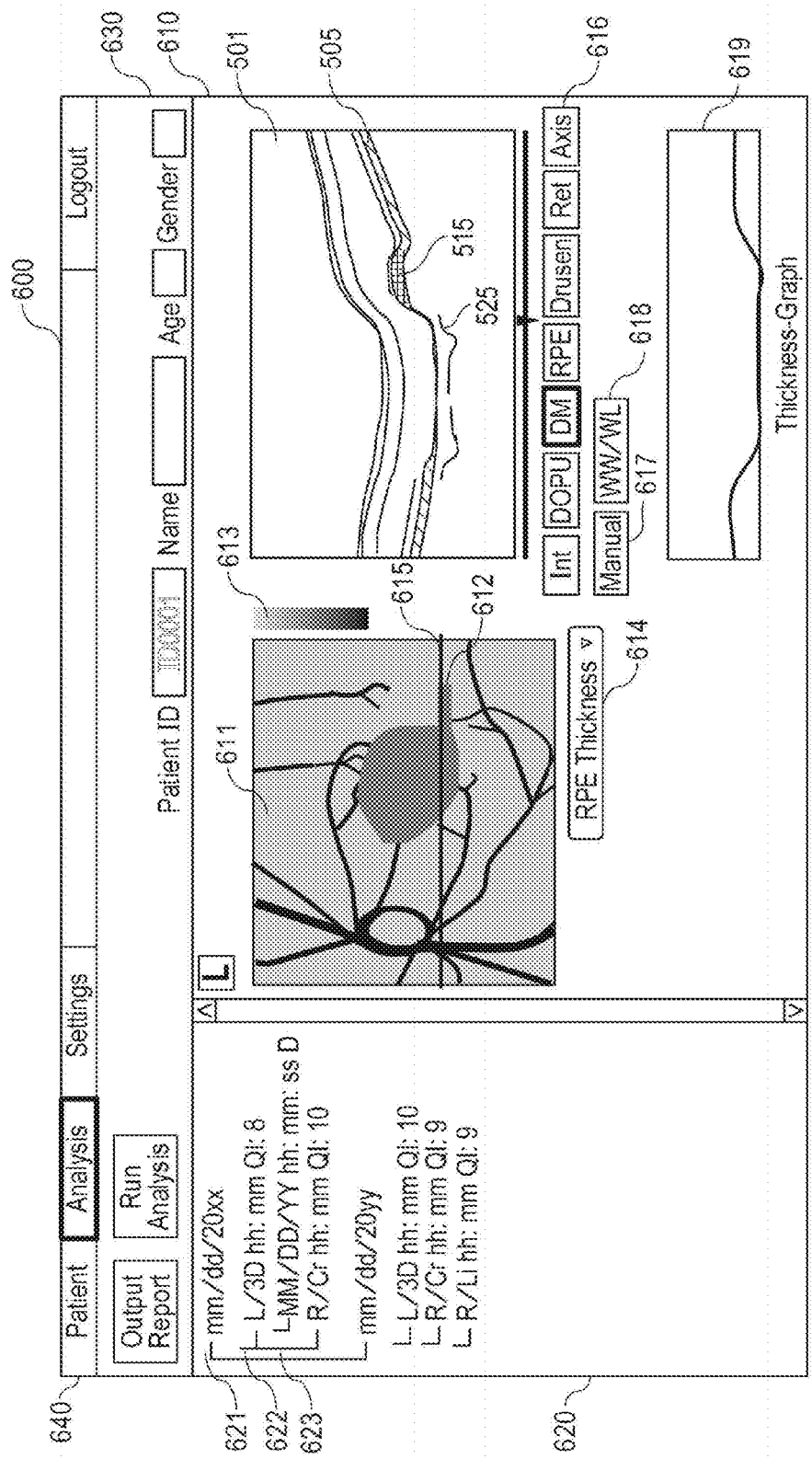

[Fig. 7A]
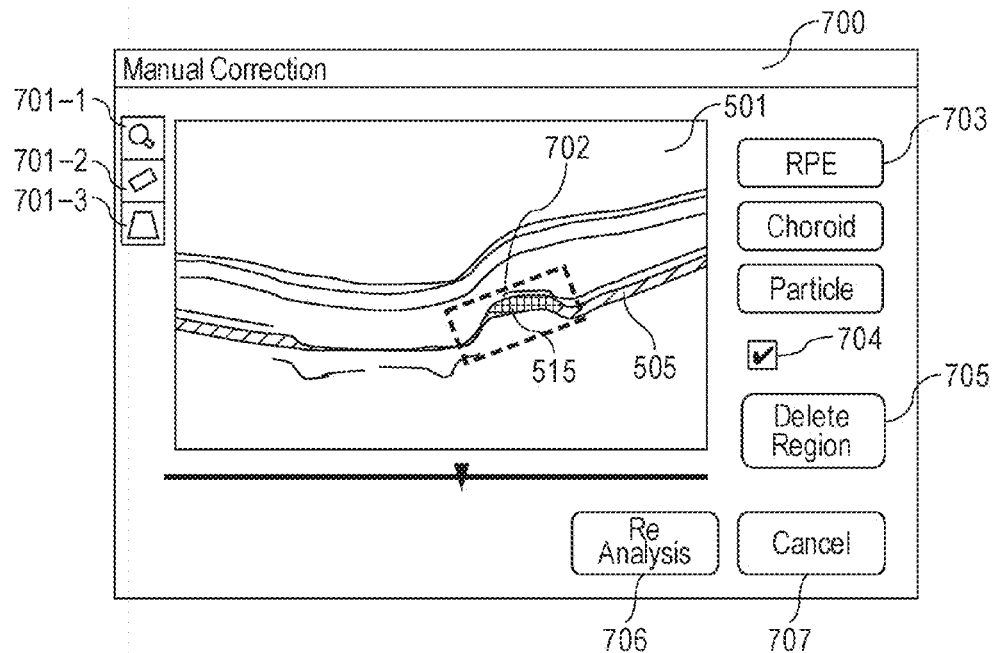
[Fig. 7B]
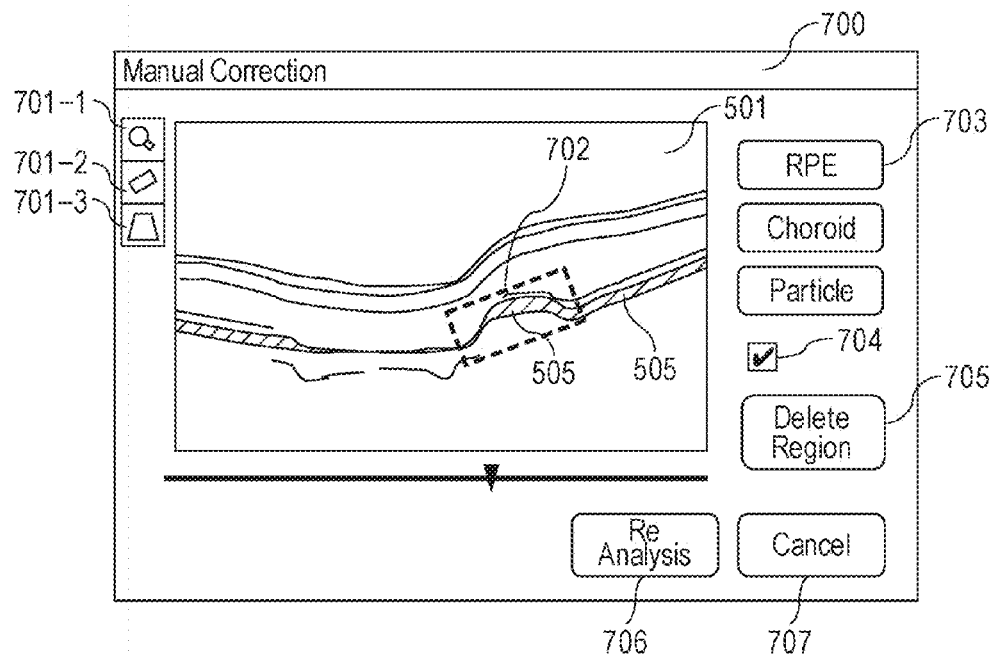

[Fig. 8]
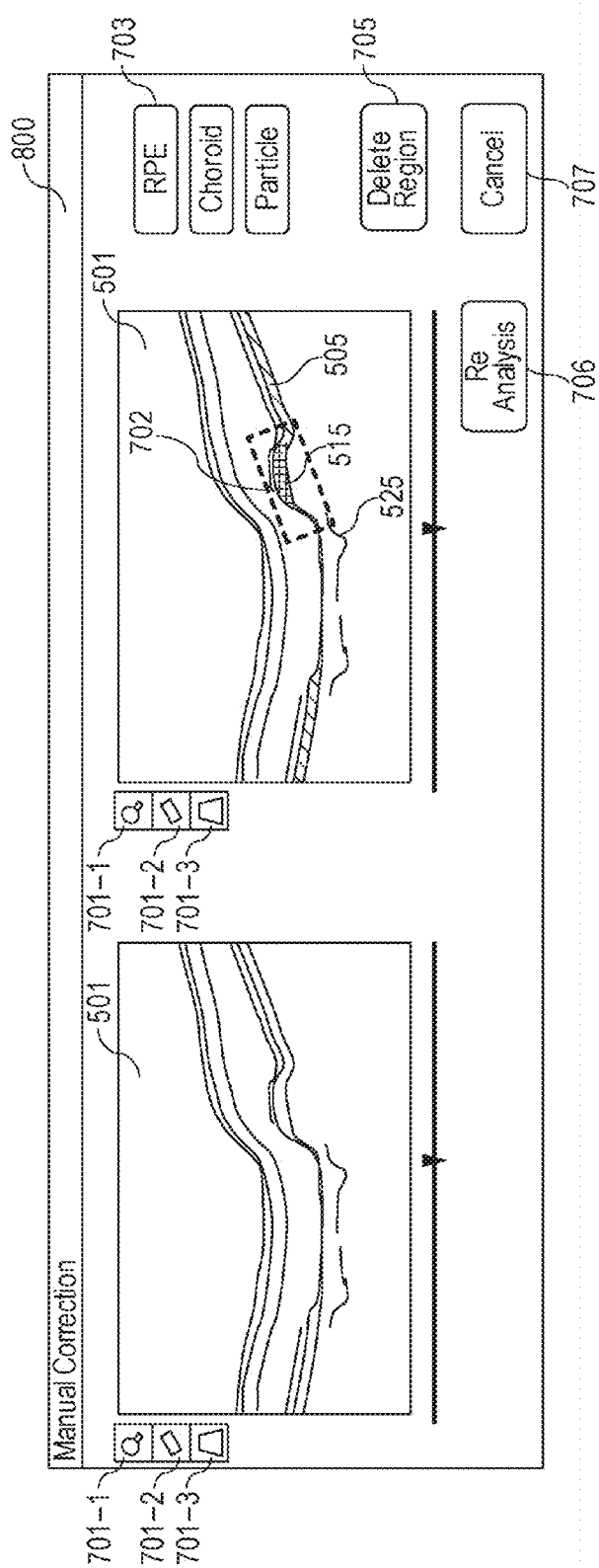

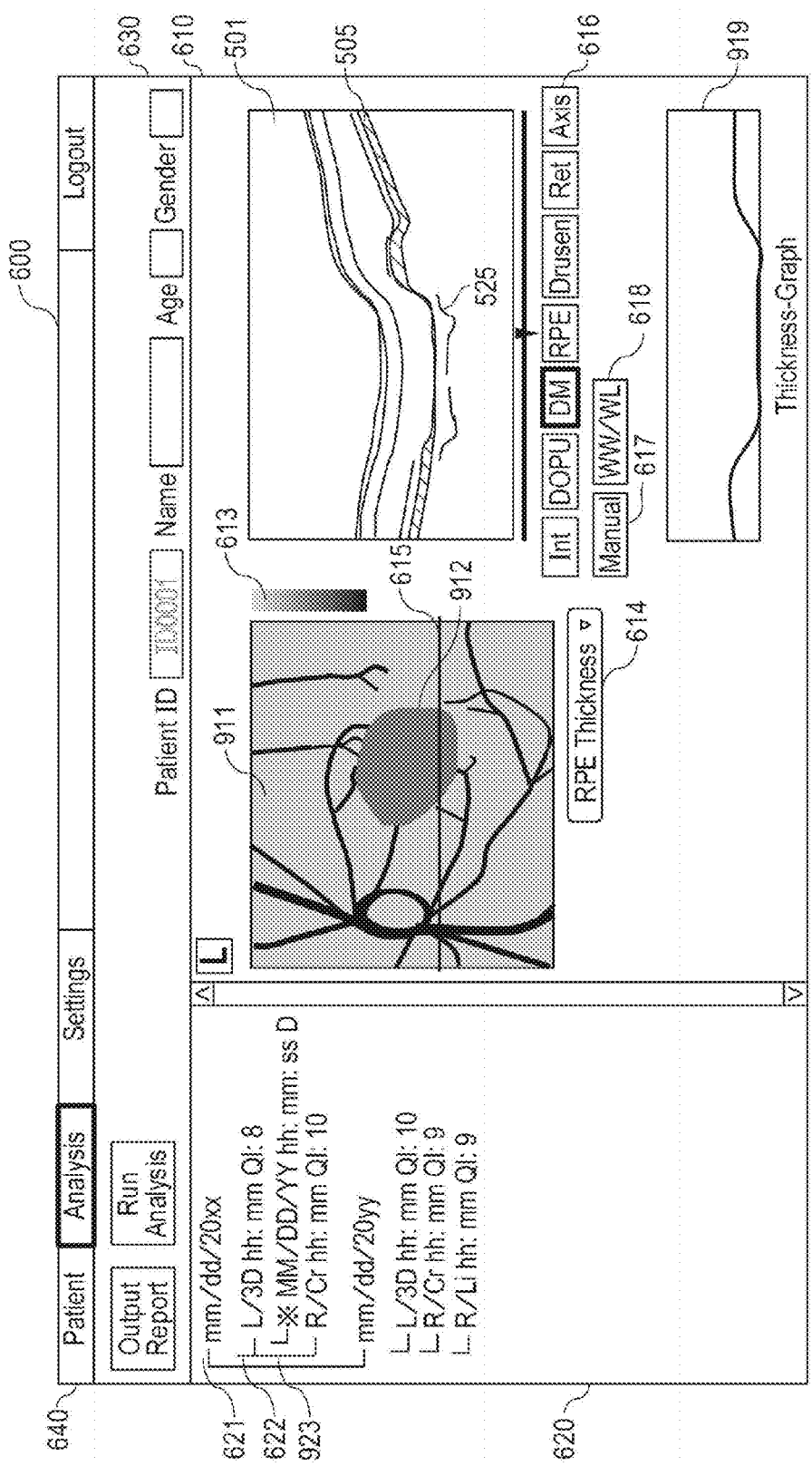
[Fig. 9]

IMAGE PROCESSING APPARATUS, IMAGE PROCESSING METHOD, AND PROGRAM

TECHNICAL FIELD

The present invention relates to an image processing apparatus and an image processing method for processing a tomographic image of a subject's eye, and a program.

BACKGROUND ART

Optical coherence tomography (OCT) utilizing multi-wavelength light wave interference may obtain a tomographic image of a sample (particularly, a fundus) with high resolution. In recent years, in OCT apparatuses for ophthalmology, obtainment of a functional OCT image obtained by imaging optical characteristics, movements, and the like of fundus tissues is attempted in addition to a normal OCT image obtained by imaging shapes of fundus tissues.

Polarization sensitive OCT which is one of such functional OCTs performs imaging using a polarization parameter (retardation and orientation) which is one of the optical characteristics of fundus tissues. The polarization sensitive OCT may form a polarization sensitive OCT image using the polarization parameter and perform detection and segmentation of fundus tissues. The polarization sensitive OCT divides interfering light into two linearly-polarized light beams which are orthogonal to each other and detects the linearly-polarized light beams using light modulated into circularly-polarized light as measurement light used to observe a sample so as to generate a polarization sensitive OCT image (refer to PTL 1).

Furthermore, in NPL1, depolarized regions extracted from a polarization sensitive OCT image are classified into an RPE region and a choroid region. Here, "depolarization" is an index representing a degree of cancellation of polarization in a subject. The depolarization is seen to be caused by random changing of a direction and a phase of polarization due to reflection of measurement light in fine structures (melanin, for example) in tissues, for example. First, a depolarized region is extracted from a polarization sensitive OCT image, and a curve of an RPE region is estimated in the extracted depolarized region. Then a portion which is positioned far from the estimated curve to a deep side or a shallow side in a depth direction is discriminated (classified) as a choroid region. Here, according to NPL1, different colors are used for displaying the RPE region and the choroid region in the polarization sensitive OCT image.

CITATION LIST

Patent Literature

PTL 1: International Publication No. WO 2010/122118A1

Non Patent Literature

NPL 1: Baumann et. al. "Segmentation and quantification of retinal lesions in age-related macular degeneration using polarization-sensitive optical coherence tomography" Journal of Biomedical optics February 2010

SUMMARY OF INVENTION

Technical Problem

According to an embodiment of the present invention, there is provided an image processing apparatus including a detection unit configured to detect a depolarized region in a polarization tomographic image of a subject's eye, an estimation unit configured to estimate a curve using the extracted depolarized region, a discrimination unit configured to discriminate the extracted depolarized region as a region including the estimated curve and a region which is discontinuous with the region including the estimated curve, and a correcting unit configured to correct at least a portion of a result of the discrimination representing the discontinuous region to a result of discrimination representing another region.

According to another embodiment of the present invention, there is provided an image processing method including detecting a depolarized region in a polarization tomographic image of a subject's eye, estimating a curve using the extracted depolarized region, discriminating the extracted depolarized regions as a region including the estimated curve and a region which is discontinuous with the region including the estimated curve, and correcting at least a portion of a result of the discrimination representing the discontinuous region to a result of discrimination representing another region.

Further features of the present invention will become apparent from the following description of exemplary embodiments with reference to the attached drawings.

BRIEF DESCRIPTION OF DRAWINGS

FIG. 1 is a diagram schematically illustrating an entire configuration of an image processing apparatus according to an embodiment.

FIG. 2A is a diagram illustrating a luminance image of an optic disk portion generated by a signal processor.

FIG. 2B is a diagram illustrating a retardation image of the optic disk portion generated by the signal processor.

FIG. 2C is a diagram illustrating a retardation map of the optic disk portion generated by the signal processor.

FIG. 2D is a diagram illustrating a birefringence map of the optic disk portion generated by the signal processor.

FIG. 2E is a diagram illustrating a DOPU image of the optic disk portion generated by the signal processor.

FIG. 3A is a processing flow according to the embodiment.

FIG. 3B is the processing flow according to the embodiment.

FIG. 4A is a diagram illustrating image analysis according to the embodiment.

FIG. 4B is a diagram illustrating the image analysis according to the embodiment.

FIG. 4C is a diagram illustrating the image analysis according to the embodiment.

FIG. 4D is a diagram illustrating the image analysis according to the embodiment.

FIG. 4E is a diagram illustrating the image analysis according to the embodiment.

FIG. 4F is a diagram illustrating the image analysis according to the embodiment.

FIG. 5A is a diagram illustrating image analysis according to the embodiment.

FIG. 5B is a diagram illustrating the image analysis according to the embodiment.

FIG. 5C is a diagram illustrating the image analysis according to the embodiment.

FIG. 5D is a diagram illustrating the image analysis according to the embodiment.

FIG. 5E is a diagram illustrating the image analysis according to the embodiment.

FIG. 5F is a diagram illustrating the image analysis according to the embodiment.

FIG. 6 is a diagram illustrating display in a display screen of a display unit included in the image processing apparatus according to the embodiment.

FIG. 7A is a diagram illustrating manual correction according to the embodiment.

FIG. 7B is a diagram illustrating the manual correction according to the embodiment.

FIG. 8 is a diagram illustrating manual correction according to the embodiment.

FIG. 9 is a diagram illustrating display in the display screen of the display unit included in the image processing apparatus according to the embodiment.

DESCRIPTION OF EMBODIMENT

In general, depolarized regions extracted from a polarization sensitive OCT image are classified into an RPE region and a choroid region. Furthermore, the RPE region and the choroid region in the polarization sensitive OCT image are displayed in different colors.

Here, discrimination (classification) of the RPE region and the choroid region may fail when signal intensity is degraded due to cataract or the like or when a lesion is generated in a fundus in a case of a subject's eye having illness.

The present invention provides an image processing apparatus and an image processing method which allow an operator to correct a result obtained by automatically classifying depolarized regions into a plurality of types of region (a plurality of regions) with ease.

The image processing apparatus of this embodiment includes a detection unit which detects depolarized regions in a polarization tomographic image of a subject's eye. Furthermore, the image processing apparatus of this embodiment includes a classifying unit which classifies the detected depolarized regions into a plurality of types of region. Furthermore, the classifying unit may classify the detected depolarized regions into a plurality of regions. For example, the classifying unit classifies (discriminates) a region corresponding to an RPE estimation curve which is an example of a first region into an RPE region. Furthermore, the classifying unit classifies (discriminates) a region which is separated from the RPE region, which is an example of discontinuous region (a region which is not continuous with the RPE region), and which is located on a shallow side relative to the RPE estimation curve into a particle region which is an example of a second region. Moreover, the classifying unit classifies (discriminates) a region which is separated from the RPE region (a region which is not continuous with the RPE region) and which is located on a deep side relative to the RPE estimation curve into a choroid region which is an example of a third region. Note that the particle region and the choroid region will be described in detail hereinafter.

The image processing apparatus of this embodiment further includes a display control unit which displays a plurality of display forms corresponding to the plurality of classified types in the display unit in a state in which the display forms are superposed on the polarization tomographic image. Furthermore, the display control unit may display the plurality of classified regions in a distinguishable manner in a state in which the classified regions are superposed on the polarization tomographic image. For example, the display control unit displays the polarization tomographic image such that the RPE region is displayed in red, the particle region is displayed in blue, and the choroid region is displayed in lime green.

The image processing apparatus according to this embodiment further includes a correcting unit which corrects a type of region corresponding to a display form specified by the operator to another type of region (a correct type of region specified by the operator). Furthermore, the correcting unit may correct a display state corresponding to a region specified by the operator (the correct region specified by the operator) to a display state corresponding to another region. Specifically, at least a portion of a discontinuous region (or at least one of the second and third regions) may be displayed in accordance with a result of the correction performed by the correcting unit. Accordingly, a result of the automatic classification of depolarized regions into a plurality of types of region may be corrected by the operator with ease. A case where an algorithm in which DOPU is not calculated in a region having pixel values of a tomographic luminance image which are lower than a threshold value is employed is taken as an example. In this case, a region which is dark due to shadows of blood vessels in an RPE region and the like are determined as a region having a luminance value lower than the threshold value. Therefore, the RPE region is not continuous (that is, the RPE region is divided) in the region having a luminance value lower than the threshold value in the RPE region. Accordingly, the RPE region is not detected with high accuracy even using a DOPU image in some cases. Here, it is likely that a region separated from the RPE region is automatically classified into a type of region different from the RPE region. Furthermore, a case where a region which is a portion of an RPE region and which is separated from the RPE region is detected since intensity of a polarization tomographic image of a subject's eye having a curved RPE caused by to lesion is low, for example, is taken as an example. Here, it is likely that the detected region separated from the RPE region is automatically classified into a type of region different from the RPE region. As described above, even when it is determined that the region is different from the RPE region even though the region is the RPE region, the operator may easily correct a display form for the region into a display form for an appropriate region, that is, a display form for the RPE region. Hereinafter, an embodiment of the present invention will be described in detail with reference to the accompanying drawings.

Entire Configuration of Apparatus

FIG. 1 is a diagram schematically illustrating an entire configuration of an image processing apparatus according to this embodiment. This apparatus includes a polarization sensitive OCT (PS-OCT) 100 which is an example of a light interference tomographic apparatus, a polarization sensitive scanning laser opthalmoscope (PS-SLO) 140 utilizing polarization, an anterior ocular segment imaging unit 160, an internal fixation lamp 170, and a controller 200. In a state in which the internal fixation lamp 170 is turned on so that the subject's eye gazes the internal fixation lamp 170, alignment of the apparatus is performed using an image of an anterior eye segment of a subject observed by the anterior ocular segment imaging unit 160. After the alignment is completed, an image of a fundus is captured using the PS-OCT 100 and the PS-SLO 140. Note that the image processing apparatus may be connected to the light interference tomographic apparatus in a communication available manner or may be incorporated in the light interference tomographic apparatus in an integrated manner.

Configuration of PS-OCT 100

A configuration of the PS-OCT 100 will be described. A light source 101 is a super luminescent diode (SLD) light source which is a low coherent light source and emits light having a center wavelength of 850 nm and a bandwidth of 50 nm, for example. Although the SLD is used as the light source 101, any light source, such as an amplified spontaneous emission (ASE) light source, may be employed as long as the light source is capable of emitting low coherent light. Light emitted from the light source 101 is guided to a fiber coupler 104 having a polarization maintaining function through a polarization maintaining (PM) fiber 102 and a polarization controller 103 and is divided into measurement light (or OCT measurement light) and reference light (or reference light corresponding to the OCT measurement light). The polarization controller 103 controls a state of polarization of the light emitted from the light source 101 so as to obtain linearly-polarized light. A division ratio of the fiber coupler 104 is 90:10 ((reference light):(measurement light)).

The measurement light obtained through the division is emitted from a collimator 106 as parallel light through a PM fiber 105. The emitted measurement light reaches a dichroic mirror 111 through an X scanner 107 including a galvanometer mirror which scans a fundus Er using the measurement light in a horizontal direction, lenses 108 and 109, and a Y scanner 110 which scans the fundus Er using the measurement light in a vertical direction. The X scanner 107 and the Y scanner 110 are controlled by a driving controller 180 so that a desired region of the fundus Er (or a range for obtaining a tomographic image, a position for obtaining a tomographic image, or a position for irradiating the measurement light) is scanned using the measurement light. The dichroic mirror 111 is characterized by reflecting light having a wavelength of 800 nm to 900 nm and allowing other light to pass.

The measurement light reflected by the dichroic mirror 111 is transmitted through a lens 112 to a λ/4 polarization plate 113 (an example of a polarization control member) which is inclined by 45° so that a phase of the measurement light is shifted by 90° and is subjected to polarization control so that circularly-polarized light is obtained. Note that the inclination of the λ/4 polarization plate 113 is preferably an angle corresponding to an inclination of a polarization division surface of a fiber coupler 123 incorporating a polarized beam splitter relative to an optical axis, for example (an example of an arrangement state). The λ/4 polarization plate 113 is preferably attachable in a light path. For example, the λ/4 polarization plate 113 may be mechanically configured such that the λ/4 polarization plate 113 is rotated around a rotation axis which is parallel to the optical axis. By this, a small apparatus capable of performing switching between an SLO optical system and a PS-SLO optical system with ease may be realized. Furthermore, a small apparatus capable of performing switching between an OCT optical system and a PS-OCT optical system with ease may be realized.

Here, light which is incident on the subject's eye is subjected to polarization control so as to obtain circularly-polarized light by disposing the λ/4 polarization plate 113 in an inclination manner by 45°. However, the circularly-polarized light may not be obtained in the fundus Er due to characteristics of the subject's eye. Therefore, the inclination of the λ/4 polarization plate 113 may be finely controlled by the driving controller 180.

The measurement light which has been subjected to the polarization control so that circularly-polarized light is obtained is focused on a retina layer of the fundus Er through an anterior eye segment Ea of an eye which is the subject by a focus lens 114 disposed on a stage 116. The measurement light which irradiates the fundus Er is reflected and scattered by retina layers and returns to the fiber coupler 104 through the light path described above.

On the other hand, the reference light divided by the fiber coupler 104 is emitted as parallel light from a collimator 118 through a PM fiber 117. The emitted reference light is, similarly to the measurement light, subjected to polarization control in a λ/4 polarization plate 119 disposed in an inclination manner by 22.5° relative to P polarized light toward S polarized light. The reference light is reflected by a mirror 122 disposed on a coherence gate stage 121 through a dispersion compensation glass 120 and returns to the fiber coupler 104. That is, the reference light passes the λ/4 polarization plate 119 twice so that linearly-polarized light returns to the fiber coupler 104.

The coherence gate stage 121 is controlled by the driving controller 180 so as to cope with differences among lengths of eyeballs of examiners. The measurement light and the reference light which return to the fiber coupler 104 are combined with each other so as to obtain interfering light (combined light) to be incident on the fiber coupler 123 incorporating a polarization beam splitter, and the interfering light is divided into light beams having different polarization directions (P polarized light and S polarized light in this embodiment) by a division ratio of 50:50.

The P polarized light is transmitted through a PM fiber 124 and a collimator 130, divided by a grating 131, and received by a lens 132 and a line camera 133. Similarly, the S polarized light is transmitted through a PM fiber 125 and a collimator 126, divided by a grating 127, and received by a lens 128 and a line camera 129. The gratings 127 and 131 and the line cameras 129 and 133 are disposed so as to correspond to directions of the S polarized light and the P polarized light, respectively. The light received by the line cameras 129 and 133 is output as electric signals corresponding to light intensities and received by a signal processor 190 (an example of a tomographic image generation unit). Although the λ/4 polarization 113 controls the inclination using a polarization beam splitter as a reference, the λ/4 polarization plate 113 may control the inclination relative to a straight line which connects a center of an optic disk of the fundus and a center of a macula. Furthermore, the same effect is obtained even when the polarization beam splitter and the λ/4 polarization plates 113 and 119 are controlled using a vertical direction as a polarization reference.

Configuration of PS-SLO 140

A configuration of the PS-SLO 140 will be described. A light source 141 is a semiconductor laser, and in this embodiment, emits light having a center wavelength of 780 nm. Measurement light (or SLO measurement light) emitted from the light source 141 is transmitted through a PM fiber 142 to a polarization controller 145 which performs polarization control on the measurement light so as to obtain linearly-polarized light and emitted from a collimator 143 as parallel light. The emitted measurement light passes a hole portion of a hole mirror 144 and reaches a dichroic mirror 154 through a lens 155, an X scanner 146 including a galvanometer mirror which scans the fundus Er using the measurement light in a horizontal direction, lenses 147 and 148, and a Y scanner 149 which scans the fundus Er using the measurement light in a vertical direction. The X scanner 146 and the Y scanner 149 are controlled by the driving controller 180 so that a desired range of the fundus Er is scanned using the measurement light. The dichroic mirror 154 is characterized by reflecting light having a wavelength of 760 nm to 800 nm and allowing other light to pass.

The linearly-polarized measurement light which is reflected by the dichroic mirror 154 reaches the fundus Er through the light path which is the same as the PS-OCT 100. The measurement light which irradiates the fundus Er is reflected and scattered by the fundus Er and reaches the hole mirror 144 through the light path described above. The light reflected by the hole mirror 144 is transmitted through a lens 150 to a polarization beam splitter 151 which divides the light into light beams having different polarization directions (P polarized light and S polarized light in this embodiment), and the light beams are received by avalanche photodiodes (APDs) 152 and 153, converted into electric signals, and received by the signal processor 190 (an example of a fundus image generation unit). Here, a position of the hole mirror 144 is conjugated with a position of a pupil of the subject's eye, and light which passes a pupil peripheral portion in the measurement light reflected and scattered after being irradiated to the fundus Er is reflected by the hole mirror 144. Although the PM fibers are used together with the PS-OCT and the PS-SLO in this embodiment, the same configuration and the same effect may be obtained when polarized light is controlled by a polarized light controller in a single mode fiber (SMF).

Anterior Ocular Segment Imaging Unit 160

The anterior eye segment imaging unit 160 will be described. The anterior eye segment imaging unit 160 irradiates the anterior eye segment Ea using an illumination light source 115 including LEDs 115-a and 115-b which emit illumination light having a wavelength of 1000 nm. The light reflected by the anterior eye segment Ea is transmitted through the lens 114, the λ/4 polarization plate 113, the lens 112, and the dichroic mirrors 111 and 154 to a dichroic mirror 161. The dichroic mirror 161 is characterized by reflecting light having a wavelength of 980 nm to 1100 nm and allowing light having other wavelengths to pass. The light reflected by the dichroic mirror 161 is transmitted through lenses 162, 163, and 164 to an anterior eye segment camera 165. The light received by the anterior eye segment camera 165 is converted into an electric signal to be supplied to the signal processor 190.

Internal Fixation Lamp 170

The internal fixation lamp 170 will be described. The internal fixation lamp 170 includes an internal fixation lamp display unit 171 and a lens 172. The internal fixation lamp display unit 171 is formed by a plurality of light emitting diodes (LDs) arranged in a matrix. Lighting positions of the light emitting diodes are changed depending on a portion to be imaged under control of the driving controller 180. Light emitted from the internal fixation lamp display unit 171 is guided to the subject's eye through the lens 172. The light emitted from the internal fixation lamp display unit 171 has a wavelength of 520 nm and a desired pattern is displayed under control of the driving controller 180.

Controller 200

The controller 200 which controls the entire apparatus will be described. The controller 200 includes the driving controller 180, the signal processor 190, a display control unit 191, and a display unit 192. The driving controller 180 controls the various units as described above. The signal processor 190 includes an image generation unit 193, a region detection unit 194, and a classifying unit 195. The signal processor 190 performs generation of an image, analysis of the generated image, and generation of visualization information on a result of the analysis in accordance with signals output from the line cameras 129 and 133, the APDs 152 and 153, and the anterior eye segment camera 165. A correcting unit 196 corrects a type of region corresponding to a display form specified by the operator to another type of region (a correct type specified by the operator). The generation and the analysis of an image and the like will be described in detail later.

The display control unit 191 causes the display unit 192 to display images generated by the tomographic image generation unit and the fundus image generation unit which are obtained by a tomographic image obtaining unit (not illustrated) and a fundus image obtaining unit (not illustrated) in a display screen of the display unit 192 (a liquid crystal display or the like). Note that image data generated by the signal processor 190 may be transmitted to the display control unit 191 in a wired manner or a wireless manner. Furthermore, although the image processing apparatus is described in this embodiment, the fundus image obtaining unit may include an SLO optical system and the tomographic image obtaining unit may include an OCT optical system as an ophthalmic apparatus or an ophthalmic system according to another embodiment of the preset invention.

The display unit 192 displays a display form representing various information under control of the display control unit 191 as described below. Note that image data supplied from the display control unit 191 may be transmitted to the display unit 192 in a wired manner or a wireless manner. Furthermore, although the display unit 192 or the like is included in the controller 200, the present invention is not limited to this and the display unit 192 or the like may be provided separately from the controller 200. Moreover, the display control unit 191 and the display unit 192 may be integrally configured as a device (tablet) which may be carried by a user. In this case, a display unit has a touch panel function so that an operation of moving a display position of an image, an operation of enlarging or reducing a size of the image, an operation of changing an image to be displayed, and the like may be performed on the touch panel.

Image Processing

Next, the generation of an image performed by the image generation unit 193 will be described.

Generation of Tomographic Image and Generation of Fundus Image

The image generation unit 193 generates two tomographic images based on polarization components (a tomographic image corresponding to first polarized light and a tomographic image corresponding to second polarized light) by performing a reconstruction processing used in general spectral domain OCT (SD-OCT) on interfering signals output from the line cameras 129 and 133. First, the image generation unit 193 removes fixed pattern noise from the interfering signals. The removal of the fixed pattern noise is performed by extracting fixed pattern noise by averaging a plurality of detected A-scan signals and subtracting the extracted fixed pattern noise from the input interfering signals. Subsequently, the image generation unit 193 converts wavelengths of the interfering signals into wavenumbers and generates tomographic signals (or tomographic signals representing polarization states) by performing Fourier transform. By performing the process described above on the two interfering signals having different polarization components, two tomographic images are generated.

Furthermore, the image generation unit 193 generates two fundus images based on the polarization components (or a tomographic image corresponding to the first polarized light and a tomographic image corresponding to the second polarized light) by arranging the signals output from the APDs 152 and 153 in synchronization with driving of the X scanner 146 and the Y scanner 149.

Generation of Luminance Image

The image generation unit 193 generates luminance images from the two tomographic signals described above. The luminance images are basically the same as tomographic images generated by general OCTs, and pixel values r of the luminance images are calculated from tomographic signals $A_H$ and $A_V$ obtained by the line cameras 129 and 133 in accordance with Expression 1.

[Math. 1]

$$r=\sqrt{A_H^2+A_V^2} \qquad \text{Expression 1}$$

Similarly, fundus luminance images are generated from the two fundus images.

FIG. 2A is a diagram illustrating a luminance image of an optic disk portion.

Generation of Retardation Image

The image generation unit 193 generates a retardation image using the tomographic images having the polarization components which are orthogonal to each other.

Values δ of pixels of the retardation image are obtained by digitizing phase differences between vertical polarization components and horizontal polarization components in positions of the pixels included in the tomographic image and are calculated using the tomographic signals $A_H$ and $A_V$ in accordance with Expression 2.

[Math. 2]

$$\delta = \arctan\left[\frac{A_V}{A_H}\right] \qquad \text{Expression 2}$$

FIG. 2B is a diagram illustrating a retardation image (or a tomographic image representing a phase difference of polarized light) of the optic disk portion generated as described above, and the image is obtained by calculating Expression 2 on B-scan images. In FIG. 2B, a portion in which a phase difference is generated in the tomographic image is displayed in color, and of a deep color portion corresponds to a small phase difference whereas a light color portion corresponds to a large phase difference. Therefore, by generating the retardation image, a layer having birefringence may be recognized.

Generation of Retardation Map

The image generation unit 193 generates a retardation map from a retardation image obtained from a plurality of B-scan images. First, the image generation unit 193 detects a retinal pigment epithelium (RPE) in the B-scan images. Since the RPE is characterized by cancelling polarization, the image generation unit 193 checks distribution of retardation in a range from an inner limiting membrane (ILM) to a point which does not include the RPE along a depth direction of A-scans and sets a maximum value as representative values of the retardation in the A-scans. The image generation unit 193 performs the process described above on all retardation images so as to generate a retardation map.

FIG. 2C is a diagram illustrating a retardation map of the optic disk portion. In FIG. 2C, a deep color portion corresponds to a small phase difference whereas a light color portion corresponds to a large phase difference. In the optic disk portion, a layer having birefringence is a retina nerve fiber layer (RNFL), and the retardation map represents a phase difference caused by the birefringence of the RNFL and a thickness of the RNFL. Therefore, a portion having a large thickness of the RNFL has a large phase difference whereas a portion having a small thickness of the RNFL has a small phase difference. Accordingly, using the retardation map, a thickness of the RNFL of the entire fundus may be recognized and is used for diagnosis of glaucoma.

Generation of Birefringence Map

The image generation unit 193 linearly approximates a value of a retardation δ in a range from the ILM and the RNFL in each of the A-scan images of the retardation image generated as described above and determines an inclination of the value as birefringence in a position of the retina in the A-scan image. The image generation unit 193 performs this process on all the obtained retardation images so as to generate a map representing birefringence. FIG. 2D is a diagram illustrating a birefringence map of the optic disk portion. Since a value of birefringence is directly mapped in the birefringence map, the birefringence map may be obtained as change of birefringence when a fiber construction is changed even in a case where a thickness of the RNFL is not changed.

Generation of DOPU Image

The image generation unit 193 calculates a Stokes vector S for each pixel using the obtained tomographic signals $A_H$ and $A_V$ and a phase difference ΔΦ between the tomographic signals $A_H$ and $A_V$ in accordance with Expression 3.

[Math. 3]

$$S = \begin{pmatrix} I \\ Q \\ U \\ V \end{pmatrix} = \begin{pmatrix} A_H^2 + A_V^2 \\ A_H^2 - A_V^2 \\ 2A_H A_V \cos\Delta\phi \\ 2A_H A_V \sin\Delta\phi \end{pmatrix} \qquad \text{Expression 3}$$

Note that the phase difference ΔΦ is calculated as "ΔΦ=$\Phi_V$−$\Phi_H$" using phases $\Phi_H$ and $\Phi_V$ of the signals obtained when the two tomographic images are calculated.

Next, the image generation unit 193 sets windows having a length of approximately 70 μm in a substantially main scanning direction of the measurement light and a length of approximately 18 μm in a substantially depth direction of the measurement light in the B-scan images. Thereafter, the image generation unit 193 averages elements of the Stokes vectors calculated for individual pixels in accordance with Expression 3 in the individual windows. Then the image generation unit 193 calculates degrees of polarization uniformity (DOPU) of polarized light in the windows in accordance with Expression 4.

[Math. 4]

$$\text{DOPU}=\sqrt{Q_m^2+U_m^2+V_m^2} \qquad \text{Expression 4}$$

Here, "$Q_m$", "$U_m$", and "$V_m$" represent values obtained by averaging elements Q, U, and V of the Stokes vectors in the windows. This process is performed on all the windows included in the B-scan image so as to generate a DOPU image (or a tomographic image representing a degree of polarization uniformity) of the optic disk portion illustrated in FIG. 2E.

The DOPU is a numeric value representing a degree of polarization uniformity. The DOPU is a numeric value near 1 in portions in which polarization is maintained and is a numeric value smaller than 1 in portions in which polarization is cancelled. In a structure inside a retina, the RPE is characterized by cancelling a polarization state, and therefore, a value of the DOPU is smaller in a portion corresponding to the RPE in the DOPU image when compared with other regions. In FIG. 2E, a light color portion 210 represents the RPE and a deep color portion 220 represents the retina layer region in which the change is maintained. Since the DOPU image is obtained by imaging a layer which cancels polarization, such as the RPE, even when the RPE is deformed due to disease, an image of the RPE is reliably obtained when compared with a case where luminance change is used.

Note that, in this specification, the tomographic images corresponding to the first polarized light and the second polarized light described above, the retardation image, the DOPU image, and the like are referred to as "tomographic images representing polarization states" where appropriate. Furthermore, in this specification, the retardation map and the birefringence map described above and the like are referred to as "fundus images representing polarization states".

Processing Operation

Next, a processing operation of the image processing apparatus will be described. In this processing, a result of discrimination of a depolarizing region in a polarization sensitive OCT image is checked and correction is performed in a case where an error occurs in the discrimination result. FIGS. 3A and 3B are flowcharts illustrating the processing operation of the image processing apparatus.

Step S301: Obtainment of Subject's Eye Information

In step S301, a subject's eye information obtaining unit, not illustrated, externally obtains an examinee identification number as information for identifying the subject's eye. Then, the subject's eye information obtaining unit obtains information on the subject's eye stored in a storage unit, not illustrated, in accordance with the examinee identification number. Here, the information on the subject's eye includes personal information including a name, a gender, an age, and a history of illness, image data including a fundus image and a tomographic image, and analysis data of image analysis and the like.

Step S302: Imaging and Image Generation

An operator specifies an imaging instruction button by a cursor displayed on a screen using an instruction device (not illustrated), such as a mouse, and issues an instruction by a clicking operation or the like so as to capture a tomographic image. Note that the mouse of this embodiment includes a sensor which detects a movement signal generated when a body of the mouse is moved in a plane by a hand of the operator, two mouse buttons including a left mouse button and a right mouse button which detect pressing of the buttons by the hand of the operator, and a wheel mechanism which is rotatable back and forth and right and left disposed between the two left and right mouse buttons. Furthermore, the instruction device may have a display unit having a touch panel function so as to issue an imaging instruction on a touch panel or may have a joystick disposed on a body of the device so as to issue an imaging instruction by the joystick. In the imaging, the light source 101 and the light source 141 emit measurement light, light returning from the fundus Er is received by the line cameras 129 and 133 and the APDs 152 and 153, and the image generation unit 193 generates images as described above.

Step S303: Image Analysis

The region detection unit 194 performs various analysis on the images generated by the image generation unit 193. Here, the region detection unit 194 detects a depolarized region which is a region including depolarizing material (DM) in the DOPU image. The depolarized region corresponds to an RPE region, a drusen region, a geographic atrophy (GA) region. This detection will be described with reference to FIG. 3B and FIGS. 4A to 4F.

Step S331: Detection of Depolarized Region

FIGS. 4A to 4F are diagrams illustrating the detection of a depolarized region in the DOPU image. A reference numeral 401 of FIG. 4A denotes a luminance image, and a reference numeral 402 of FIG. 4B denotes a DOPU image which corresponds to the luminance image of FIG. 4A and which is obtained by the DOPU calculation described above. First, a depolarized region in the DOPU image 402 is obtained. In the DOPU image 402, a depolarized region has a value smaller than 1. Therefore, by performing a threshold value process on the DOPU image (using a threshold value of 0.75, for example), a region in which polarization is maintained and a region in which polarization is cancelled may be distinguished from one another. A depolarized region 403 obtained in this way is illustrated in FIG. 4C.

Step S332: RPE Estimation

Next, discrimination of an RPE region is performed on the depolarized region 403. This discrimination will be described with reference to FIG. 4D. FIG. 4D is a graph including an RPE estimation curve 404 (represented by a dotted line in FIG. 4D) used for discriminating the RPE in the depolarized region 403. Here, a case where the estimation curve 404 is obtained as a quadric curve is described as an example. An initial curve is set so as to pass a largest region of the depolarized region 403, and coefficient parameters (a, b, and c) of the curve are estimated using the robust estimation method (M estimation or the like). In this way, a curve may be obtained. The method for estimating a curve is not limited to this and estimation of an N-order curve may be employed or a spline curve may be employed.

Step S333: First Analysis?

In step S333, it is determined whether first analysis is performed or analysis after correction (re-analysis) is performed. In a case of the first analysis, the process proceeds to step S334 since discrimination of a depolarized region has not been performed. After second analysis onwards, the process proceeds to step S338. The second analysis onwards will be described in detail when an operation in step S306 is described, and an operation in step S334 will be described here.

Step S334: Discrimination (Classification)

The classifying unit 195 discriminates (classifies) an RPE region from other depolarized regions (a choroidal tissue and a particle region) in accordance with the RPE estimation curve 404 obtained in step S332. Specifically, the classifying unit 195 classifies depolarized regions into a plurality of types of region. A depolarized region existing in a region where the RPE estimation curve 404 passes is determined as an RPE region. In this way, a continuous depolarized region in which the RPE estimation curve 404 passes is determined as an RPE region 405 (a hatched portion in FIGS. 4E and 4F). Specifically, if the RPE estimation curve 404 passes a portion in a continuous depolarized region, a portion around the region is determined as the RPE region 405. Then, a depolarized region which is not continuous with the RPE region 405 and which exists in a deeper portion relative to the RPE region 405 is determined as a choroid (choroid tissue) region and a depolarized region existing in a shallower portion relative to the RPE region 405 is determined as a particle region. The RPE region 405 obtained in this way is illustrated in FIG. 4E. In FIG. 4F, a case where the RPE region 405 is superposed on the luminance image 401 is illustrated.

Step S335: Generation of Mask Image

Next, a mask is generated in a region other than the RPE in accordance with results of the discrimination obtained in step S334 and step S338. Specifically, an image only including the RPE region is generated. Note that it is not necessarily the case that a mask image is generated since labeling is performed in the discrimination performed before the generation of a mask image, and a drusen calculation may be performed without generating a mask image.

Step S336: Drusen Calculation

Next, a drusen calculation is performed using the RPE image generated in step S335. Positions of deepest portions of the RPE image in individual A-scan images or discrete A-scan images are detected as drusen positions. A drusen curve is obtained by smoothly connecting the detected positions by a spline function or the like. Drusen generally has a convex shape. Therefore, a reference RPE base curve is obtained in order to obtain an area and a volume of the drusen. A minimum RPE base curve including the convex shape of the drusen may be obtained by calculating a convex hull of the obtained drusen curve. Note that the RPE estimation curve described above and the RPE base curve obtained here are different from each other.

Step S337: Generation of Map (Enface) Image

Finally, map (enface) images are generated for individual regions discriminated in step S334. Note that, in this embodiment, a DM thickness map, an RPE thickness map, a drusen thickness map, and a GA map are generated. Here, a method for generating a map will be described taking the RPE thickness map as an example. In a case of the RPE thickness map, the number of pixels including the RPE is counted for each A-scan in the RPE tomographic image generated in step S335. A thickness of the RPE may be obtained by multiplying the number of pixels counted as the RPE by a pixel resolution (μm/pixel) in a depth direction.

Similar processes are performed for the other maps. In a case of the DM thickness map, the total number of pixels included in the depolarized region obtained in step S331 is multiplied by the pixel resolution. In a case of the drusen thickness map, the total number of pixels included in a portion between the drusen curve obtained in step S336 and the RPE base curve is multiplied by the pixel resolution. In a case of the GA map, the RPE thickness map is binarized by a certain threshold value (a threshold value of 10 μm, for example) instead of a thickness. When GA is developed, the RPE becomes defective, and accordingly, when the RPE thickness map is binarized, the RPE exists in normal portions and the RPE does not exist in portions in which the RPE is defective due to the GA. Therefore, an area of the GA may be obtained using the defective regions.

In FIGS. 4A to 4F, the general discrimination of depolarized regions is described. Next, a case where discrimination of a depolarized region fails will be described with reference to FIGS. 5A to 5F in order to describe an example of manual correction. In FIGS. 5A to 5F, a case where a depolarized region in a PRE region is separated and an RPE estimation curve does not pass the separated depolarized region is illustrated as an example. FIGS. 5A to 5C and FIG. 5F are the same as FIGS. 4A to 4C and FIG. 4F, respectively, and therefore, descriptions thereof are omitted. A reference numeral 514 of FIG. 5D denotes a portion where a depolarized region is separated, a reference numeral 503 denotes the depolarized region, and a reference numeral 504 denotes an RPE estimation curve obtained by the same method in step S332. A reference numeral 505 of FIG. 5E which is a hatched portion is a region determined as an RPE region, a reference numeral 515 which is a shaded portion is a region determined as a particle region, and a reference numeral 525 is a region determined as a choroid region. Hereinafter, a description is made with reference to the example illustrated in FIGS. 5A to 5F. Note that, although the case where the discrimination results are differently displayed by hatching and shading is described as an example in this embodiment, the present invention is not limited to this. Different colors may be used such that an RPE region is represented by red, a particle region is represented by blue, and a choroid region is represented by lime green.

Step S304: Display

In the image generation unit 193 and the region detection unit 194 included in the signal processor 190, when the generation and the analysis of the images are terminated, the display control unit 191 generates output information in accordance with results of the generation and the analysis and outputs the output information to the display unit 192 which displays the output information.

FIG. 6 is a diagram illustrating display performed by the display unit 192 of this embodiment. In FIG. 6, a reference numeral 600 denotes a window displayed in the display unit 192, and the window 600 includes display regions 610, 620, 630, and 640. In the display region 610, a region 611 displaying a fundus plane image and an analysis map (enface) image, a color bar 613 for displaying a thickness of a map in color, a section 614 for selecting the fundus plane image and the analysis map, an index 615 displaying a position of a tomographic image in the map, a tomographic image 501, results 505, 515, and 525 of discrimination of depolarized regions, a tomographic image selection section 616, a manual correction selection section 617, a WW/WL selection section 618, and a thickness graph 619 are displayed. In the section 614 for selecting the fundus plane image and the analysis map, a pseudo SLO, the DM thickness map, the RPE thickness map, the drusen thickness map, the GA map, the retardation map, the birefringence map, and the like may be displayed in a switching manner. In the tomographic image selection section 616, the luminance image, the DOPU image, the DM image, the RPE image, the drusen image, the retardation image, and an axis orientation image may be displayed in a switching manner. Here, as the DM image, the RPE image, and the drusen image, an image obtained by superposing an image obtained from a depolarized region (described above in step S303) on the luminance image is displayed. Specifically, in the case of the DM image, depolarized regions are discriminated by different colors and all the depolarized regions are displayed in an overlapping manner. Note that the case where the plurality of types of depolarized region represented by different colors are displayed in the state in which the depolarized regions are superposed on a polarization tomographic image is merely an example, and any state may be employed as long as different types of region are displayed by different display forms so as to be discriminated from one to another. In the case of the RPE image, only the RPE region discriminated from depolarized regions is displayed in an overlapping manner. In the case of the drusen image, the drusen curve and the RPE base curve are displayed in an overlapping manner.

In the display region 620, a tree of inspection data is displayed. A reference numeral 621 denotes a date of imaging, a reference numeral 622 denotes imaging information (a left eye or a right eye, a scanning pattern, and a time of imaging), and a reference numeral 623 denotes a time of analysis and an analysis mode. In the display region 630, patient information (identification information, a name, an age, and a gender) is displayed. Note that the patient information is not limited to these and other information may be displayed as the patient information. In the display region 640, information for identifying a screen being operated is displayed. In this embodiment, a patient data management screen, an analysis screen, and a setting screen are displayed. In this embodiment, the display region 640 has not only the display function but also a selection function, and when one of sections in the display region 640 is selected, switching of a function is realized.

In this embodiment, the analysis map 611 corresponds to the RPE thickness map, the thickness graph 619 corresponds to an RPE thickness, and the DM image is displayed as a tomographic image, for example. The thickness graph 619 is associated with the analysis map 611. Note that, although types of image to be displayed as the analysis map 611 and the tomographic image may be independently selected, the types may be associated with each other. For example, when the DM image is selected as the tomographic image, the DM thickness map may be displayed as an analysis map image. A thickness of the RPE thickness map generated by the result 505 of the discrimination of a polarized region is displayed by color as represented by the color bar 613. In this embodiment, a deep color represents a thin map and a light color represents a thick map. In the RPE thickness map of FIG. 6, a deep color region 612 near a center represents a portion which does not include a region recognized as the RPE. A rectangular portion in a lower right portion in the region 612 is a portion corresponding to the result 515 of the discrimination of a depolarized region in FIG. 5E, and since the RPE region is misjudged as the particle region, the region 612 has a distorted shape.

Step S305: Correction? (Change?)

In step S305, a process of determining whether a result of the discrimination of a depolarized region is to be changed is performed. When the manual correction selection section 617 of FIG. 6 is selected, a manual correction screen 700 illustrated in FIGS. 7A and 7B is displayed. The manual correction screen 700 will now be described with reference to FIGS. 7A and 7B. FIG. 7A is a diagram illustrating a state in which manual correction has not been performed, and FIG. 7B is a diagram illustrating a state in which the manual correction has been performed. In the manual correction, when one of a plurality of display forms corresponding to the plurality of types of depolarized region is specified by the operator, the correcting unit 196 corrects (changes) a type corresponding to the specified display form to another type. The manual correction screen 700 includes a tomographic image on which the result of the discrimination of a depolarized region is superposed, icons 701 for selecting an operation on the tomographic image, a region 702 for performing the manual correction, a discrimination result instruction section 703 for instructing correction of the discrimination result, a discrimination result display specifying section 704, a region deletion specifying section 705, a re-analysis execution instruction section 706, and a cancel instruction section 707. Here, an icon 701-1 is used to specify enlargement and reduction of a size of the tomographic image, an icon 701-2 is used to specify a rectangular region, and an icon 701-3 is used to specify a polygonal region. Furthermore, the discrimination result instruction section 703 specifies a result of the discrimination as the RPE region, the choroid region, or the particle region.

In a case where a user selects a region in which a result of the discrimination of a depolarized region is to be changed, the user specifies the region in the tomographic image after selecting the icon 701-2 or the icon 701-3. It is assumed that the icon 701-2 is selected and the rectangular region 702 (denoted by a dotted line in FIGS. 7A and 7B) is set in this embodiment. The user may arbitrarily set a position, a size, and rotation of the rectangular region 702. Note that, in a case where a tomographic image representing a luminance value is to be checked before the manual correction is performed, only the luminance image is displayed by unchecking the discrimination result display specifying section 704. FIG. 7A is a diagram illustrating a case where the rectangular region 702 is set as the depolarized region 515. FIG. 7B is a diagram illustrating a case where the RPE is selected in the discrimination result instruction section 703 after the region 702 is set. As illustrated in FIG. 7B, the entire depolarized region 515 is corrected (changed) by the manual correction to the RPE region 505. In a case where the set region 702 is to be changed, the region 702 may be deleted and another region may be newly set by selecting the region deletion specifying section 705.

Although a result of discrimination is specified after a region is selected as the method for correcting a result of discrimination of a depolarized region, the present invention is not limited to this. For example, the discrimination result instruction section 703 may be selected before a region is specified. In this case, since a result of discrimination is set in the discrimination result instruction section 703, a region is automatically corrected to a region specified by the discrimination result instruction section 703 every time a region is set unless the setting is cancelled. A result of discrimination may be corrected, for example, at a timing after a size of a region is specified by performing left clicking and dragging of the mouse and the mouse operation is terminated in a case of a rectangular region or a timing when a starting point and an ending point of a polygonal region is connected to each other in a case of a polygonal region. Furthermore, a save button, not illustrated, may be pressed for saving.

In addition, instead of the specifying of the region 702, only a certain portion in the result of the discrimination of a depolarized region may be specified so that a discrimination result of an entire continuous region is corrected. For example, when a certain point of the depolarized region 515 of FIG. 7A is clicked with the left mouse button, an entire region connected to a depolarized region in a clicked coordinate may be corrected to a result specified by the discrimination result instruction section 703.

Furthermore, in a case of tomographic image data on which volume scanning is being performed, a plurality of slices are generated. In this case, even when a slice position of B-scan is changed, the region 702 set to a certain B-scan image may be maintained while another region 702 which has been set to another B-scan image may be employed.

In the manual correction screen 700, when the correction is performed and the re-analysis execution instruction section 706 is selected, the process proceeds to step S306 whereas when the cancel instruction section 707 is selected, the process proceeds to step S308. Note that a shape of a region subjected to the manual correction and the type of the discrimination result instruction section 703 of a depolarized region described above are not limited to these described above. A circular shape or an N-sided polygonal shape may be employed, and a hard exudate or the like may be specified as the type.

FIG. 8 is a diagram illustrating another form of the manual correction screen. In FIG. 8, in the manual correction screen described with reference to FIGS. 7A and 7B, the luminance tomographic image 501 and the tomographic image 501 on which the results 505, 515, and 525 of the discrimination of a depolarized region are superposed are displayed in parallel. Note that, in a case where a luminance tomographic image and a tomographic image on which results of discrimination of a depolarized region are superposed are displayed in parallel, it is preferable that slice positions are associated with each other and represent the same position.

Step S306: Image Analysis

In step S306, re-analysis is performed in accordance with a result of the manual correction. Here, the flow of FIG. 3B is performed only on corrected B-scan images. When the re-analysis is performed, only an operation in step S338 of FIG. 3B is different and the other operations are similarly performed. When the re-analysis is performed, the discrimination of a depolarized region has been performed by the manual correction, and therefore, a calculation is performed using a corrected result of the discrimination.

To attain high-speed operation, only B-scan images which have been subjected to the manual correction are changed. However, the present invention is not limited to this. In a case where the discrimination is performed using information on an adjacent B-scan image at a time of image analysis, it is preferable that the re-analysis is performed using all information required for the discrimination, and therefore, the process may be executed again on B-scan images other than the corrected B-scan images.

Step S307: Display

In step S307, a result of the correction and the re-analysis is displayed. An example of the display is illustrated in FIG. 9. In FIG. 9, a state in which analysis maps 911 and 912 and a result of discrimination of a depolarized region are corrected as a result of the manual correction is displayed. Furthermore, an index 923 represents whether correction of a result of analysis has been performed is displayed before the analysis time in the inspection data tree. Note that not only a result of a determination as to whether correction has been performed on single image volume data but also a result of a determination as to whether correction has been performed in a unit of a B-scan image may be displayed. For example, an index (an icon or the like) representing whether correction has been performed may be displayed in a unit of a B-scan image at an edge of a tomographic image of FIG. 9 or a result of a determination as to whether correction has been performed may be displayed by color in a frame of the tomographic image.

Step S308: Termination?

In step S308, checking of the analysis result and execution of termination of the manual correction are selected. After the manual correction is terminated or before a process of selecting an imaging mode is performed, the result of the manual correction obtained in the foregoing process and the result of the analysis performed by the region detection unit 194 are stored in a storage unit.

As described above, the present invention has a system in which a result of discrimination of a depolarized region in a polarization sensitive OCT image is checked, and in addition, correction is performed in a case where an error occurs in the discrimination result. Therefore, according to the present invention, the discrimination of a depolarized region may be performed, and in addition, a result of the discrimination may be appropriately stored. Note that, although the case where a depolarized region is analyzed is described in this embodiment, the present invention is not limited to this. As an image analysis mode, a drusen analysis mode, a GA analysis mode, a glaucoma analysis mode, analysis modes corresponding to diseases, a full analysis mode for executing all processes, or the like may be selected. In the glaucoma analysis mode, a mode for analyzing polarization components associated with a nerve fiber layer, such as retardation and axis orientation, may be provided, and the user may select and execute an arbitrary analysis mode.

Other Embodiments

The present invention is also realized by executing the following process. Specifically, software (or a program) which realizes the functions of the foregoing embodiment is supplied to a system or an apparatus through a network or various storage media, and a computer (or a CPU or an MPU) of the system or the apparatus reads and executes the program.

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment of the present invention, and by a method performed by the computer of the system or apparatus by, for example, reading out and executing the computer executable instructions from the storage medium to perform the functions of one or more of the above-described embodiment. The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-229912, filed Nov. 12, 2014, which is hereby incorporated by reference herein in its entirety.

The invention claimed is:

1. An image processing apparatus comprising:
a detection unit configured to detect a depolarized region in a polarization tomographic image of a subject's eye;
an estimation unit configured to estimate a curve using the detected depolarized region;
a discrimination unit configured to discriminate the detected depolarized region as a region including the estimated curve and a region which is discontinuous with the region including the estimated curve; and
a correcting unit configured to correct, in response to an instruction issued by an operator, at least a portion of a result of the discrimination representing the discontinuous region to a result of discrimination representing another region in the detected depolarized region.

2. The image processing apparatus according to claim 1, further comprising:
a display control unit configured to cause a display unit to display a region including the curve and the discontinuous region in different display forms and display in the display unit at least a portion of the discontinuous region in accordance with a result of the correction performed by the correcting unit.

3. The image processing apparatus according to claim 2, wherein, when a tomographic intensity image of the subject's eye corresponding to the polarization tomographic image and a second tomographic intensity image are displayed in the display unit, a result of correction performed by the correcting unit on the displayed second tomographic intensity image is maintained, an acquired position of the second tomographic intensity image being different from an acquired position of the tomographic intensity image.

4. The image processing apparatus according to claim 1, wherein
the discrimination unit discriminates a region including the curve as a first region and the discontinuous regions as a second region on a shallow side and a third region on a deep side relative to the estimated curve in a depth direction of the polarization tomographic image, and
the correcting unit configured to correct at least one of at least a portion of a result of the discrimination representing the second region and at least a portion of a result of the discrimination representing the third region to a result of discrimination representing another region in response to an instruction issued by the operator.

5. The image processing apparatus according to claim 4, further comprising:
a display control unit configured to cause a display unit to display the first to third regions in different display forms and display in the display unit at least one of the second and third regions in accordance with a result of the correction performed by the correcting unit.

6. The image processing apparatus according to claim 1, further comprising:
an obtaining unit configured to obtain the polarization tomographic image obtained by imaging the subject's eye using a light interference tomographic apparatus, wherein the image processing apparatus is connected in a communication available manner to the light interference tomographic apparatus including a detection unit which detects light beams which are obtained by dividing combined light obtained by combining returning light of measurement light irradiated to the subject's eye and reference light corresponding to the measurement light and which have different polarization components.

7. The image processing apparatus according to claim 1, further comprising an image generation unit configured to generate an analysis map regarding a region including the curve by using regions including the curve in the polarization tomographic image at different positions of the subject's eye and configured to generate the analysis map again after correction by the correcting unit by using a correction result regarding a type corresponding to a display form at a position corresponding to the region including the curve.

8. An image processing apparatus comprising:
a detection unit configured to detect a depolarized region in a polarization tomographic image of a subject's eye;
a classifying unit configured to classify the detected depolarized regions into a plurality of types of region;
a display control unit configured to cause a display unit to display a plurality of display forms corresponding to the plurality of classified types of region in a state in which the display forms are superposed on a tomographic intensity image of the subject's eye corresponding to the polarization tomographic image; and
a correcting unit configured to correct a type of region corresponding to at least a part of one of the display forms specified by an operator to another type of region among the plurality of classified types of region.

9. The image processing apparatus according to claim 8, wherein the display control unit causes the display unit to display a display form corresponding to the corrected type of region in a state in which the display form is superposed on the tomographic intensity image.

10. The image processing apparatus according to claim 8, wherein the correcting unit performs the correction when the operator specifies the other type of region from among the plurality of types of region after specifying one of the plurality of display forms.

11. The image processing apparatus according to claim 8, wherein the correcting unit performs the correction when the operator specifies one of the plurality of display forms after specifying the other type of region from among the plurality of types of region.

12. The image processing apparatus according to claim 8, wherein, when the tomographic intensity image and a second tomographic intensity image are displayed in the display unit, a result of correction performed by correction unit on the displayed second tomographic intensity image is maintained, an acquired position of the second tomographic intensity image being different from acquired position of the polarization tomographic image.

13. The image processing apparatus according to claim 8, further comprising a tomographic image acquisition unit configured to acquire the tomographic intensity image and the polarization tomographic image by processing a common optical coherence tomography (OCT) signal of return light and reference light, the return light returning from the subject's eye irradiated with measuring light, wherein the acquired tomographic intensity image and the acquired polarization tomographic image correspond to each other in terms of position of portion of the subject's eye on image.

14. The image processing apparatus according to claim 8, wherein
the classifying unit automatically classifies a plurality of regions in the detected depolarized regions into the plurality of types of region including a type of lesion of the subject's eye,
the display control unit causes the display unit to display the tomographic intensity image in a state in which the display forms are superposed at a plurality of positions corresponding to the plurality of regions,
the correcting unit corrects a type corresponding to a display form at a position specified by the operation from among the plurality of positions in the tomographic intensity image into the another type specified by the operator.

15. The image processing apparatus according to claim 14, wherein
upon specifying one of the plurality of positions by the operator after the operator has specified the another type, the correcting unit corrects the type corresponding to the display form at the specified position into the specified another type, and
the display control unit causes the display unit to display the tomographic intensity image in a state in which the display form at the specified position has been changed into a display form corresponding to the specified another type.

16. The image processing apparatus according to claim 15, wherein
in a case where one of the plurality of positions has been specified by the operator earlier, upon specifying the another type by the operator after the operator has specified the one of the plurality of positions, the correcting unit corrects the type corresponding to the display form at the specified position into the specified another type, and
in a case where the another type has been specified by the operator earlier, upon specifying one of the plurality of positions by the operator after the operator has specified the another type, the correcting unit corrects the type corresponding to the display form at the specified position into the specified another type.

17. The image processing apparatus according to claim 14, wherein
wherein, upon specifying the another type by the operator after the operator has specified one of the plurality of positions, the correcting unit corrects the type corresponding to the display form at the specified position into the specified another type, and
wherein the display control unit causes the display unit to display the tomographic intensity image in a state in which the display form at the specified position has been changed into a display form corresponding to the specified another type.

18. The image processing apparatus according to claim 8, wherein the plurality of display forms are different colors.

19. An image processing apparatus comprising:
a detection unit configured to detect a depolarized region in a polarization tomographic image of a subject's eye;
a classifying unit configured to classify the detected depolarized regions into a plurality of regions;
a display control unit configured to cause display unit to display the plurality of classified regions in a display state in which the regions are superposed on a tomographic intensity image of the subject's eye corresponding to the polarization tomographic image in a distinguishable manner; and
a correcting unit configured to correct a display state corresponding to a region specified by an operator to a display state corresponding to another region among the plurality of classified types of region.

20. The image processing apparatus according to claim 19, wherein, when the tomographic intensity image and a second tomographic intensity image are displayed in the display unit, a result of correction performed by the correcting unit on the displayed second tomographic intensity image is maintained, an acquired position of the second tomographic intensity image being different from an acquired position of the polarization tomographic image.

21. The image processing apparatus according to claim 19, further comprising a tomographic image acquisition unit configured to acquire the tomographic intensity image and the polarization tomographic image by processing a common optical coherence tomography (OCT) signal of return light and reference light, the return light returning from the subject's eye irradiated with measuring light, wherein the acquired tomographic intensity image and the acquired polarization tomographic image correspond to each other in terms of position of portion of the subject's eye on image.

22. An image processing method comprising:
detecting a depolarized region in a polarization tomographic image of a subject's eye;
estimating a curve using the detected depolarized region;
discriminating the detected depolarized regions as a region including the estimated curve and a region which is discontinuous with the region including the estimated curve; and
correcting, in response to an instruction issued by an operator, at least a portion of a result of the discrimination representing the discontinuous region to a result of discrimination representing another region in the detected depolarized region.

23. A non-transitory computer-readable medium storing a program that causes a computer to execute various steps of the image processing method set forth in claim 22.

24. An image processing method comprising:
detecting a depolarized region in a polarization tomographic image of a subject's eye;
classifying the detected depolarized regions into a plurality of types of region;
causing a display unit to display a plurality of display forms corresponding to the plurality of classified types of region in a state in which the display forms are superposed on a tomographic intensity image of the subject's eye corresponding to the polarization tomographic image; and
correcting a type of region corresponding to at least a part of one of the display forms specified by an operator to another type of region among the plurality of classified types of regions.

25. A non-transitory computer-readable medium storing a program that causes a computer to execute various steps of image processing method set forth in claim 24.

26. An image processing method comprising:
detecting a depolarized region in a polarization tomographic image of a subject's eye;
classifying the detected depolarized regions into a plurality of regions;
causing a display unit to display the plurality of classified regions in a display state in which the regions are superposed on a tomographic intensity image of the subject's eye corresponding to the polarization tomographic image in a distinguishable manner; and
correcting a display state corresponding to a region specified by an operator to a display state corresponding to another region among the plurality of classified types of region.

27. A non-transitory computer-readable medium storing a program that causes a computer to execute various steps of image processing method set forth in claim 26.

* * * * *